US00PP32764P2

(12) United States Plant Patent
Danziger

(10) Patent No.: US PP32,764 P2
(45) Date of Patent: Jan. 19, 2021

(54) ***SUTERA* PLANT NAMED 'DBACSCGWI'**

(50) Latin Name: *Sutera cordata*
Varietal Denomination: DBACSCGWI

(71) Applicant: Gavriel Danziger, Beit Dagan (IL)

(72) Inventor: Gavriel Danziger, Beit Dagan (IL)

(73) Assignee: Danziger Flower Farm

( * ) Notice: Subject to any disclaimer, the term of this patent is extended or adjusted under 35 U.S.C. 154(b) by 0 days.

(21) Appl. No.: 16/602,456

(22) Filed: Oct. 8, 2019

(51) Int. Cl.
*A01H 5/02* (2018.01)
*A01H 6/00* (2018.01)

(52) U.S. Cl.
USPC ..... Plt./485
CPC ..... *A01H 6/00* (2018.05)

(58) Field of Classification Search
USPC ..... Plt./485
CPC ..... A01H 5/02
See application file for complete search history.

*Primary Examiner* — Kent L Bell
(74) *Attorney, Agent, or Firm* — Cassandra Bright

(57) ABSTRACT

A new and distinct *Sutera* cultivar named 'DBACSCGWI' is disclosed, characterized by abundant extra-large white flowers and a semi-trailing habit. Plants are of medium-strong vigor, well branched and begin flowering early. The new variety is a *Sutera*, normally produced as an outdoor garden or container plant.

2 Drawing Sheets

Figure 1:
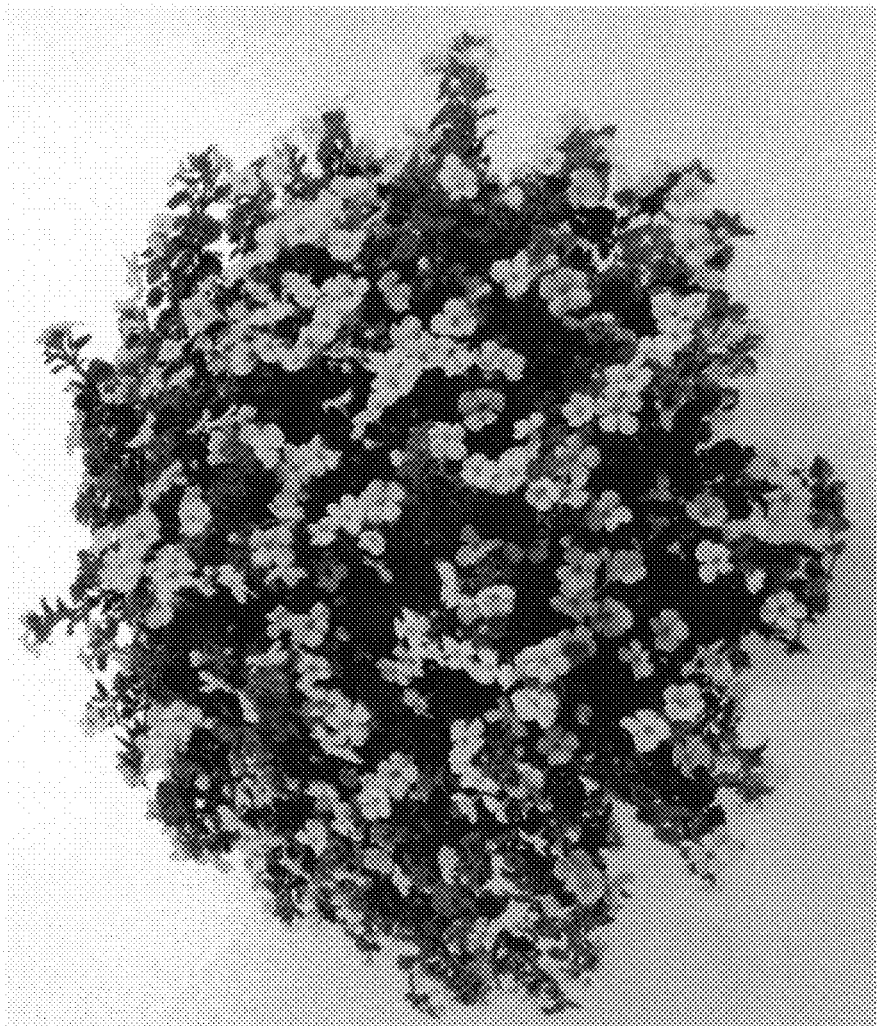

Latin name of the genus and species: *Sutera cordata*.
Variety denomination: 'DBACSCGWI'.

BACKGROUND OF THE INVENTION

The new *Sutera* cultivar is a product of a planned breeding program conducted by the inventor, Gavriel Danziger, in Moshav Mishmar Hashiva, Israel. The objective of the breeding program was to produce new *Sutera* varieties for ornamental commercial applications. The open pollination resulting in this new variety was made during April of 2011.

The seed parent is the, unpatented, proprietary variety referred to as *Sutera* 'cv. 10-1853'. The pollen parent is unknown as it was an open pollination breeding program. The new variety was discovered in February of 2012 by the inventor in a group of seedlings resulting from the 2011 open pollination, in a research greenhouse in Moshav Mishmar Hashiva, Israel. Date of first sale was Nov. 1, 2018, occurring in the United States. This sale was made directly by the inventor or one who obtained the claimed invention directly or indirectly from the inventor. This sale and all public disclosures made between Nov. 1, 2018 and the filing of this application fall within the exception allowed under 102(b)(1).

Asexual reproduction of the new cultivar was performed by vegetative cuttings. This was first performed at a research greenhouse in Moshav Mishmar Hashiva, Israel in February of 2012 and has shown that the unique features of this cultivar are stable and reproduced true to type in more than 20 successive generations.

SUMMARY OF THE INVENTION

The cultivar 'DBACSCGWI' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DBACSCGWI' These characteristics in combination distinguish 'DBACSCGWI' as a new and distinct *Sutera* cultivar:

1. Semi-trailing growth habit.
2. Extra-large white flowers.
3. Very branched.
4. Early, abundant flowering.
5. Medium-strong vigor.

Plants of the new cultivar 'DBACSCGWI' are similar to plants of the seed parent, *Sutera* 'cv. 10-1853' in most horticultural characteristics, however, plants of the new cultivar 'DBACSCGWI' differ in the following;

1. The new variety is semi-trailing, while the parent is trailing.
2. The new variety has larger flowers than the parent variety.
3. The new variety flowers more abundantly than the parent variety.
4. The new variety is very well branched. The parent variety is medium branched.
5. The new variety is more vigorous than the parent variety.

COMMERCIAL COMPARISON

Plants of the new cultivar 'DBACSCGWI' are comparable to the patented commercial variety *Sutera* 'DANCOP37', U.S. Plant Pat. No. 23,835. The two *Sutera* varieties are similar in most horticultural characteristics; however, the new variety 'DBACSCGWI' differs in the following:

1. The comparison variety is more compact than the new variety
2. Flower color of the comparison variety is blue, while the new variety has white flowers
3. The comparison variety has medium vigor, while the new variety has medium-strong vigor.

Plants of the new cultivar 'DBACSCGWI' can also be comparable to the patented commercial variety *Sutera* 'DCOPGPKHRT', U.S. Plant Pat. No. 27,655. The two *Sutera* varieties are similar in most horticultural characteristics; however, the new variety 'DBACSCGWI' differs in the following:

1. The comparison variety has a mounded growth habit, while the new variety has a semi-trailing growth habit.
2. Flower color of the comparison variety is light pink with a violet center, while the new variety has white flowers.
3. The comparison variety is more compact than the new variety.

BRIEF DESCRIPTION OF THE PHOTOGRAPHS

The accompanying photograph in FIG. 1 illustrates in full color a typical plant of 'DBACSCGWI' grown in a greenhouse, in a 13 cm pot. Age of the plant photographed is approximately 3 months old from a rooted cutting.

Figure 2:
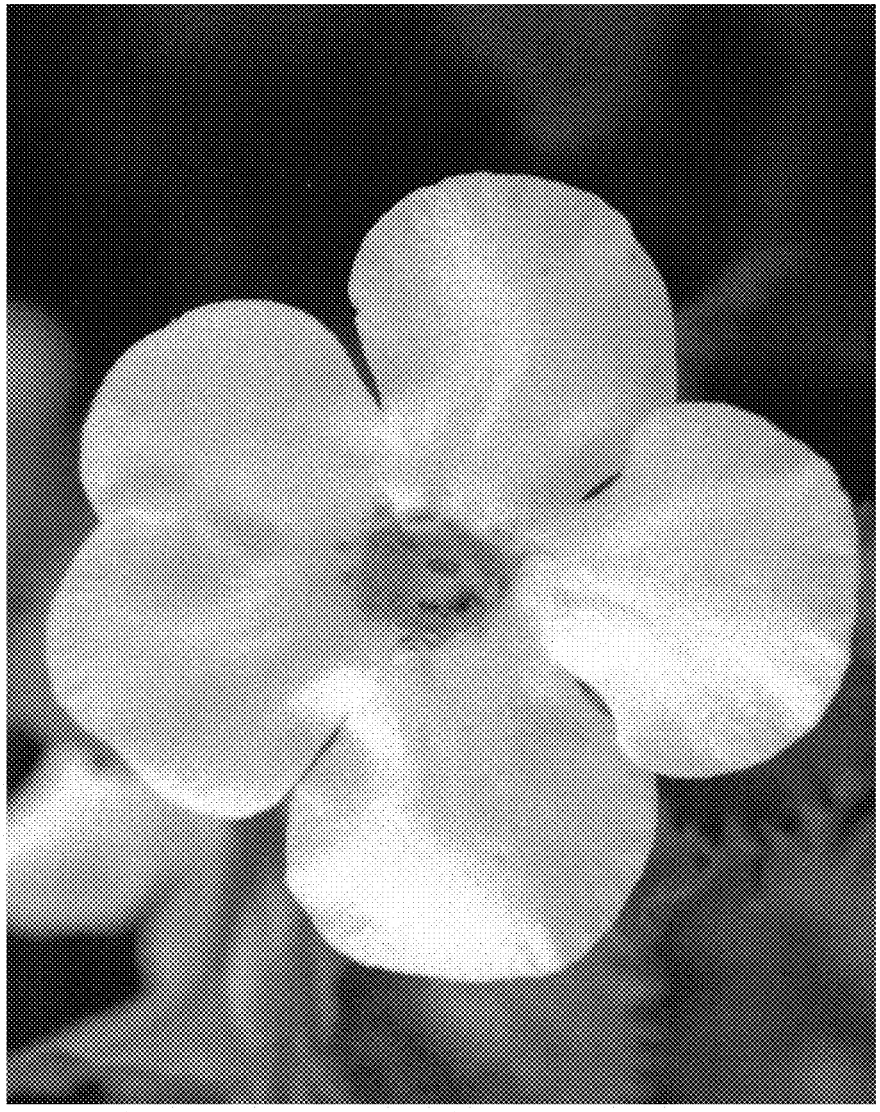

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DBACSCGWI' plants grown in the Winter to Spring in moderate climate in a greenhouse, in Moshav Mishmar Hashiva, Israel. The growing temperature ranged from 15° C. to 26° C. during the day and from 13° C. to 16° C. during the night. General light conditions are normal sunlight and numerical values represent averages of typical plant types.

Botanical classification: *Sutera cordata* 'DBACSCGWI'.

PROPAGATION

Time to initiate roots: 7-10 days at approximately 20° C.
Root description: Fine, fibrous roots.

PLANT

Age of plant described: Approximately 3 months from rooted cutting.
Container size of the plant described: 13 cm.
Growth habit: Semi-trailing.
Height: Approximately 15 cm.
Plant spread: Approximately 60 cm.
Growth rate: Medium.
Characteristics of primary lateral branches:
- *Quantity*.—About 8.
- *Form*.—Cylindrical.
- *Length*.—About 25 cm.
- *Diameter*.—About 0.3 cm.
- *Color*.—RHS Green 137C.
- *Texture*.—Velvety.
- *Strength*.—Good.

Internode length: About 2 cm.

FOLIAGE

Leaf:
- *Arrangement*.—Opposite.
- *Quantity*.—Approximately 50 per branch.
- *Average length*.—3 cm.
- *Average width*.—2.8 cm.
- *Shape of blade*.—Ovate.
- *Apex*.—Obtuse.
- *Base*.—Acuminate.
- *Margin*.—Serrate.
- *Texture of top surface*.—Velvety.
- *Texture of bottom surface*.—Velvety.
- *Pubescence*.—Slightly pubescent all surfaces.
- *Aspect*.—About 90° to branch.
- *Color*.—Young foliage upper side: RHS Green N137A. Young foliage under side: RHS Green 137B. Mature foliage upper side: RHS Green N137B. Mature foliage under side: RHS Green 137B.
- *Venation*.—Type: Pinnate. Venation color upper side: RHS Green N137B. Venation color under side: RHS Green 137B.
- *Petiole*.—Length: About 0.5 cm. Diameter: About 0.2 cm. Color: RHS Green 137B.
- *Texture*.—Slightly velvety.

FLOWER

Natural flowering season: All year round in Israel.
Days to flowering from rooted cutting: About 45.
Inflorescence and flower type and habit: Axillary, solitary, salverform single flowers.
Rate of flower opening: 3 to 5 days from bud to fully opened flower.
Flower longevity on plant: About 7 days.
Persistent or self-cleaning: Persistent.
Bud:
- *Shape*.—Spatulate.
- *Length*.—About 1.5 cm.
- *Diameter*.—About 0.5 cm.
- *Color*.—RHS Yellow-White 158C.

Flower size:
- *Diameter*.—About 2.8 cm.
- *Length*.—About 1.5 cm.

Corolla tube:
- *Tube diameter*.—About 0.4 cm.
- *Tube length*.—About 1.0 cm.
- *Tube texture*.—Slightly velvety.
- *Tube color*.—Near Yellow-Orange 17A.

Flower throat:
- *Throat diameter*.—About 4 mm.
- *Throat texture*.—Velvety pubescent.
- *Throat color*.—Near RHS Yellow-Orange 17A.

Corolla/petals:
- *Arrangement*.—Symmetric.
- *Lobe length*.—About 1.1 cm.
- *Lobe width*.—About 1.2 cm.
- *Quantity*.—5.
- *Texture*.—Velvety.
- *Lobe apex*.—Rounded.
- *Lobe shape*.—Rounded.
- *Margin*.—Entire.
- *Aspect*.—About 90° to the tube.

Color:
*When opening*.—Upper surface: RHS White NN155C. Lower surface: RHS White NN155C.
*Fully opened*.—Upper surface: RHS White NN155C. Lower surface: RHS White NN155C.
*Visible corolla tube color*.—RHS Yellow-Orange 17A.
Calyx/sepals:
*Quantity per flower*.—5.
*Shape*.—Linear.
*Length*.—About 0.6 cm.
*Width*.—About 0.1 cm.
*Apex*.—Acute.
*Base*.—Fused.
*Margin*.—Entire.
*Texture*.—Slightly velvety.
*Color*.—Upper Surface: RHS Green 137B. Lower Surface: RHS Green 137C.
Peduncle: None.
Pedicel:
*Length*.—Approximately 1.2 cm.
*Diameter*.—Approximately 0.1 cm.
*Color*.—Near RHS Green 137D.
*Orientation*.—Slanted upward and outward.
*Pubescence*.—Slightly pubescent.
Fragrance: None.

REPRODUCTIVE ORGANS

Stamens:
*Number*.—4.
*Filament length*.—Approximately 1.1 cm.
Anthers:
*Shape*.—Cylindrical.
*Length*.—Approximately 0.1 cm.
*Color*.—RHS Yellow-Orange 17C.
*Pollen*.—Color: RHS Yellow-Orange 17B. Quantity: Abundant.
Pistil:
*Number*.—1.
*Length*.—About 1.4 cm.
*Style*.—Length: About 1.1 cm. Color: RHS Yellow-Green 146C.
*Stigma*.—Shape: Undulate. Color: RHS Yellow-Green 144A. Ovary Color: RHS Green 143C.

OTHER CHARACTERISTICS

Seeds and fruits: About 20 elliptic, small (1 mm long) beige seeds per one elliptic brown capsule. Minute, not accurately measured with R.H.S. chart.
Disease/pest resistance: Typical to other *Sutra cordata* varieties.
Temperature tolerance: Approximately 5° to 30° C.

What is claimed is:

1. A new and distinct cultivar of *Sutera* plant named 'DBACSCGWI' as herein illustrated and described.

* * * * *